(12) United States Patent
Bowie

(10) Patent No.: US 8,935,951 B2
(45) Date of Patent: Jan. 20, 2015

(54) TEST TOOL

(75) Inventor: Angus George Bowie, Scotland (GB)

(73) Assignee: Stats (UK) Limited, Aberdeen, Scotland (GB)

( * ) Notice: Subject to any disclaimer, the term of this patent is extended or adjusted under 35 U.S.C. 154(b) by 0 days.

(21) Appl. No.: 12/401,859

(22) Filed: Mar. 11, 2009

(65) Prior Publication Data

US 2009/0229349 A1  Sep. 17, 2009

(30) Foreign Application Priority Data

Mar. 12, 2008  (GB) .................................. 0804588.2

(51) Int. Cl.
*G01M 3/28* (2006.01)
*G01N 3/04* (2006.01)
*G01N 3/00* (2006.01)

(52) U.S. Cl.
CPC .. *G01N 3/04* (2013.01); *G01N 3/00* (2013.01); *G01N 2203/0296* (2013.01)
USPC ............................... 73/49.5; 73/49.1; 73/49.6

(58) Field of Classification Search
CPC .............................. G01M 3/2823; G01M 3/005
USPC .......................................................... 73/49.1
See application file for complete search history.

(56) References Cited

U.S. PATENT DOCUMENTS

| | | | |
|---|---|---|---|
| 3,823,605 A | 7/1974 | Schmitz et al. | |
| 3,954,005 A | 5/1976 | Edwards | |
| 4,458,522 A | 7/1984 | Toelke | |
| 5,419,184 A * | 5/1995 | Pace ................................ | 73/49.6 |
| 5,797,431 A * | 8/1998 | Adams ............................ | 138/89 |
| 6,463,791 B1 * | 10/2002 | Berube et al. .................. | 73/49.8 |
| 6,601,437 B2 * | 8/2003 | Gotowik ......................... | 73/49.8 |
| 6,976,536 B2 | 12/2005 | Simpson et al. | |
| 7,669,482 B2 | 3/2010 | Jacobs et al. | |
| 7,739,917 B2 | 6/2010 | Shuster et al. | |
| 7,874,217 B2 * | 1/2011 | Carson ............................ | 73/850 |
| 2004/0065445 A1 | 4/2004 | Abercrombie Simpson et al. | |
| 2007/0157707 A1 | 7/2007 | Garcia Gomez | |
| 2009/0229349 A1 | 9/2009 | Bowie | |

FOREIGN PATENT DOCUMENTS

| | | |
|---|---|---|
| JP | 56-18741 | 2/1981 |
| JP | 59-26033 | 2/1984 |

(Continued)

OTHER PUBLICATIONS

United Kingdom Combined Search and Examination Report dated Jul. 14, 2008.

*Primary Examiner* — Paul West
(74) *Attorney, Agent, or Firm* — Carlson, Gaskey & Olds, P.C.

(57) ABSTRACT

A test tool for use in testing a tubular component such as a pipe includes a body having first and second body portions together defining a sliding sleeve. Axially spaced sealing and gripping modules are provided, with one module located on the first body portion and another module located on the second body portion. A force-generating arrangement is provided to apply an axial test force to the tubular component via the modules. A test pressure is applied to a section of the wall of the tubular component and an axial load is applied to the wall section. Application of the axial load between the first and second modules applies the axial load to the wall section of the tubular component to facilitate strength testing of the tubular component.

28 Claims, 3 Drawing Sheets

(56) References Cited

FOREIGN PATENT DOCUMENTS

JP    2002-323419    11/2002

JP    2002323419 A  *  11/2002
RU    2150686    6/2000

* cited by examiner

TEST TOOL

REFERENCE TO RELATED APPLICATION

This application claims priority to United Kingdom Patent Application No. 0804588.2 filed Mar. 12, 2008.

FIELD OF THE INVENTION

This invention relates to a test tool and in particular, but not exclusively, to a test tool for testing the strength and pressure integrity of a tubular component.

BACKGROUND OF THE INVENTION

Many industries make use of tubular components such as pipes, tubes, pipe modules, pipelines or the like to transport fluid over distance. For example, in the oil and gas industry, a pipeline may comprise a series of pipe modules which are transported to and assembled on site via bolted or welded flange connections. Each module may also comprise a number of components coupled together. For example, a typical flange connection on a pipe section comprises a radially extending flange which is welded to an end of the pipe section, the flange being suitable for bolting or welding to a similar flange on another section of pipe.

A number of tools have been developed which permit the integrity of a section of pipe, in particular, but not exclusively, the welds of the pipe, to be tested for leakage.

In the case of a flange connection, tools have been developed which permit the flange weld to be pressure tested. For example, one tool comprises a flanged end which, on insertion of the tool into the pipe, is coupled to the flanged end of the pipe to be tested. The tool flange and pipe flange are typically bolted together to form a flange connection, though other means for securing the flange connection can be used. The tool further comprises a seal unit spaced from the flange connection, the flange and seal unit defining a volume. In use, the tool is inserted into the pipe such that the flange connection and seal unit straddle the section of the pipe and/or the weld to be tested. Pressurized fluid is inserted through a port in the tool flange into the volume, thereby applying a test pressure between the flange connection and the seal unit. The pressure of the fluid in the volume is monitored so that the integrity of the weld can be assessed.

An alternative tool is used for pressure testing an annular section of a pipe and comprises two axially spaced seals located on a body. On insertion into the pipe to be tested, the seals are energized such that the seals, the body and the pipe wall define an annular volume into which pressurized fluid may be inserted to apply a test pressure between the seals. The pressure of the fluid in the volume is monitored so that the integrity of the weld can be assessed, a drop in pressure indicating that the weld may have failed.

In each case, the tool applies a radial load to the pipe section being tested, the load being the test pressure multiplied by the area of pipe wall exposed to the test pressure. The tools are typically designed to minimize generation of axial loading by minimizing the depth of the annular volume and the test pressure generated axial loads tend to be restrained by or transferred through the tool body.

Thus, while the pressure test provided by conventional tools establishes the pressure integrity of the pipe section, they do not provide a complete assessment of the strength capability of the pipe section and/or weld to be tested.

SUMMARY OF THE INVENTION

According to a first aspect of the present invention, there is provided a method of testing a tubular component, the method comprising the steps of applying a test pressure to a section of a wall of a tubular component, and applying an axial load to said wall section.

The method may further comprise monitoring the axial load and/or applying a selected axial load to test the strength of the tubular component.

By monitoring the test pressure while applying the axial load, the strength of the tubular component may be tested.

The method may comprise applying the test pressure and axial load simultaneously. Alternatively, the test pressure and axial load may be applied sequentially.

The method may comprise providing first and second elements and engaging the first and second elements with axially spaced portions of the tubular component. The method may further comprise providing a gripping mechanism and securing the tool to the tubular component via the gripping mechanism. Application of an axial force to the first and second elements may apply the axial load to the wall section of the tubular component, for example via the gripping mechanism, to facilitate testing the strength of the tubular component.

The method may further comprise providing at least one seal element and engaging the, or each, seal element with the tubular component. A volume may be defined between the seal elements and the tubular component and the method may further comprise directing pressurized fluid into the volume to permit leak testing of the section of the tubular component.

The method may further comprise monitoring the fluid pressure within the volume to assess the integrity of the tubular component.

According to a second aspect of the present invention there is provided a test tool for use in testing a tubular component, the tool comprising first and second elements adapted to engage axially spaced portions of a tubular component, and a force-generating arrangement adapted to apply an axial test force to the tubular component via the elements.

Where traditionally test tools have sought to minimize the generation of axial loads, a tool according to embodiments of the present invention applies an axial load to the tubular component to facilitate localized strength testing of the tubular component. For example, but not exclusively, a method and a tool according to embodiments of the present invention may be used to test the strength of a tubular component, a portion of a tubular component and/or a connection such as a weld or the like.

At least one of the first and second engaging elements may be adapted to engage an interior portion of the tubular component. The tool may be adapted for location at any location within the tubular component. In particular embodiments, the tool may be adapted for location adjacent to an end of the tubular component.

Alternatively, or in addition, at least one of the first and second engaging elements may be adapted to engage an exterior portion of the tubular component.

The provision of an external engaging element may be beneficial where the tubular component is of relatively small diameter.

At least one of the first and second engaging elements may comprise a gripping or lock mechanism. In use, the first and second engaging elements may be adapted to grip the tubular component such that an axial load applied to the first and second gripping elements generates an axial load on the tubular component. In particular embodiments, the axial load may be applied between the first and second engaging elements.

The, or each, engaging element may comprise at least one gripping element adapted to engage the tubular component. The gripping element may comprise a single gripping member or alternatively the gripping element may comprise a plurality of gripping members. For example, in one embodiment the first gripping element comprises a taper lock. Alternatively, or in addition, the first gripping element may comprise a clamp, a bearing member such as ball bearings or any other suitable gripping element.

In a further alternative, the second engaging element may comprise a flange portion for engaging a flange on the tubular component.

The force-generating arrangement may comprise any suitable arrangement for applying an axial test force to the tubular component. The tool may, for example, be adapted to apply a test force up to a selected test threshold.

The force-generating arrangement may be adapted to apply a tensile force to the tubular component to test the tensile strength of the tubular component. The axial force may be directed between the first and second engaging elements, thereby seeking to push the elements apart.

In particular embodiments, the tool may comprise a body having first and second body portions, the first and second body portions being adapted for relative axial movement. The first and second body portions may be coupled together by any suitable means, for example, the first and second body portions may be coupled together by a retention bolt. The tool may further comprise a resilient member such as a retention spring. The resilient member assists in maintaining engagement between the first and second body portions, even when the tool is adapted for location on an inclined or substantially vertical tubular component. Alternatively, the first and second body portions may be adapted for separate location on the tubular component.

The first and second engaging members may define an inner void or volume and, in use, pressurized fluid may be inserted into the volume to apply the axial force to the first and second body portions.

The force-generating arrangement may be adapted to apply an axial separating force to the first and second engaging elements via separation of the body portions, thereby applying a tensile test force to the tubular component. For example, the first engaging element may be mounted on the first body portion and the second engaging element may be mounted on the second body portion such that the axial force applied to the first and second body portions is transferred to the engaging elements and in turn is transferred to the tubular component.

In particular embodiments, the force-generating arrangement may comprise a hydraulic arrangement such as a hydraulic piston arrangement or the like. Alternatively, or in addition, the force-generating arrangement may comprise a pneumatic arrangement and/or a mechanical arrangement such as a screw or the like. In the case of a mechanical arrangement, torque may be applied via the screw to generate the required axial force on the engaging elements.

At least a portion of the first and second engaging elements may be adapted to move relative to the tubular component. For example, in use, axial movement of the, or each, engaging element may be adapted to urge respective gripping elements into engagement with the tubular component. For example, pressurized fluid may be inserted into a chamber defined between the respective engaging element and the respective body portion to translate the engaging element relative to the body to urge the gripping element into engagement with the tubular component. In particular embodiments, the engaging element comprises a taper lock and movement of the engaging element engages the taper lock with the tubular component. However, it will be understood that any suitable mechanism for engaging the elements may be used, where required.

The tool also applies a radial force to the tubular component to pressure test the tubular component. For example, at least one of the first and second engaging elements shall further comprise a seal element for engaging the tubular component.

The tool defines a volume between the first and second engaging elements and the tubular component. In use, pressurized fluid is inserted into the volume to permit leak testing of the section of the tubular component to be tested. By monitoring the fluid pressure within the chamber, the integrity of the tubular component can be assessed.

The, or each, seal element may be of any suitable form. For example, in one embodiment, two axially spaced seal elements may be provided, a first seal element mounted on the first engaging element and a second seal element mounted on the second engaging element. In use, the first and second seal elements may be adapted to straddle a portion of the wall of the tubular component and permit the pressure testing of the wall portion. In particular embodiments, the tool may be adapted to straddle a weld to permit pressure testing of the weld.

In particular embodiments, the, or each, seal element may be adapted to engage the interior of the tubular component.

Alternatively, the tool may comprise one seal element located on the first engaging element and the second engaging element may comprise a flange adapted to sealingly engage a flange on the tubular component. In this embodiment, the volume may be defined between the tool flange and the seal element.

The, or each, seal element may be of any suitable construction. For example, the seal element may be an elastomeric seal element. In particular embodiments, the seal element may be a compression seal element, that is, a seal that can be energized by compressing the seal element. Compression seal elements may be preferred as these provide compliance with the tubular component even where the inner surface of the tubular component is irregular or has been subject to damage, though other seal elements may be used where appropriate.

The seal element may be set or energized by any suitable mechanism. For example, where the seal element comprises a compression seal, the seal element may be compressed at least in part by a mechanical force, a hydraulic force, a pneumatic force, a combination of these or by any other suitable means.

In use, axial movement of the respective engaging element may be adapted to compress the respective seal element, moving a sealing surface of the seal element into engagement with the tubular component.

BRIEF DESCRIPTION OF THE DRAWINGS

These and other aspects of the present invention will now be described, by way of example only, with reference to the accompanying drawings, in which.

DETAILED DESCRIPTION OF THE DRAWINGS

Figure 1:
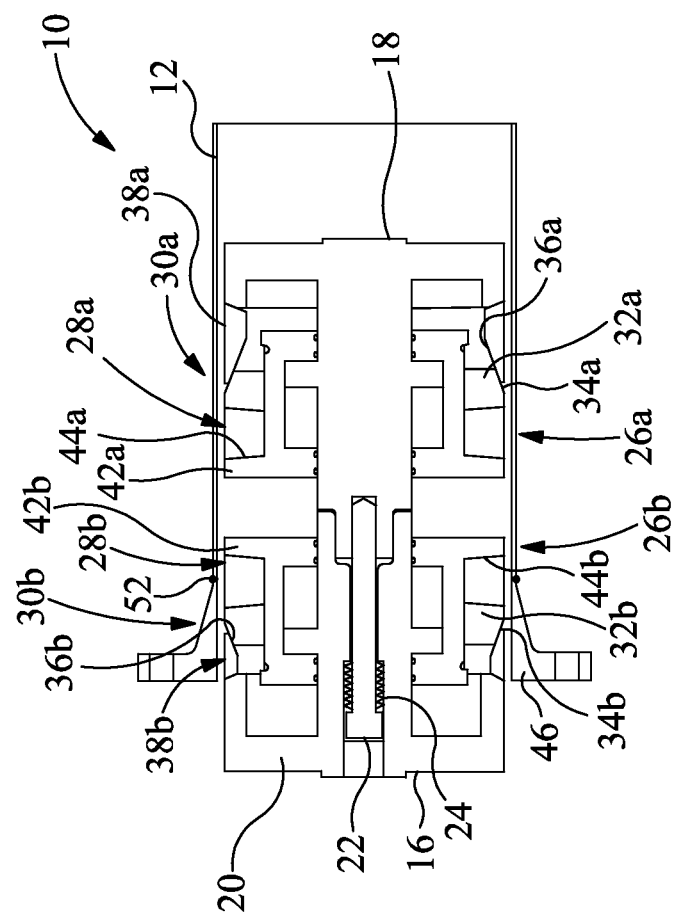
FIG. 1 is a diagrammatic cross-sectional view of a tool according to a first embodiment of the present invention, shown prior to engagement with a tubular component.
Figure 2:
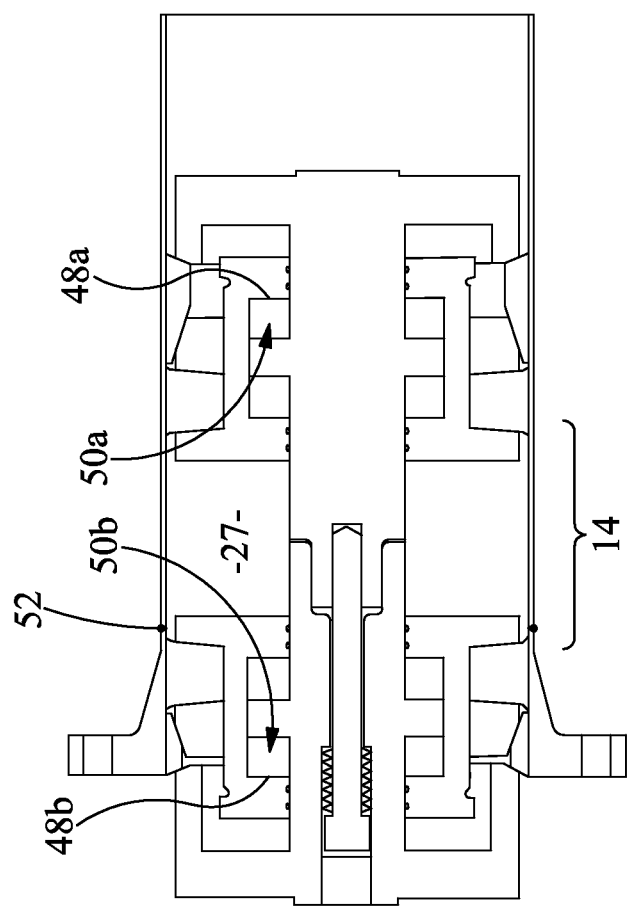
FIG. 2 is a diagrammatic cross-sectional view of the tool of FIG. 1, shown engaged with the tubular component.

In reference initially to FIGS. 1 and 2 of the drawings, there is shown a test tool 10 according to a first embodiment of the present invention. The tool 10 is adapted for location in a tubular component such as a pipe 12 and is adapted to straddle a pipe section 14 to be tested (shown most clearly in FIG. 2).

In FIG. 1, the tool 10 is shown prior to engagement with the pipe 12. The tool 10 comprises a body 16 having first and second body portions 18, 20 with an inner volume or chamber 21 defined between the body portions 18, 20. The body portions 18, 20 are adapted for relative axial movement and together define a sliding sleeve arrangement.

The body portions 18, 20 are connected together by a retention bolt in the form of a cap screw 22. In addition, a retention spring in the form of one or more disc spring 24 is provided on the cap screw 22, the screw 22 and spring 24 acting as a restraint system to resist separation of the body portions 18, 20, even where the tool 10 is located within an inclined or vertical section of the pipe 12.

The tool 10 further comprises two axially spaced engaging elements in the form of pipe sealing and gripping modules 26a, 26b and the tool is adapted to define an outer volume or chamber 27 (shown most clearly in FIG. 2) between the body 16, the modules 26a, 26b and the pipe 12.

One module 26a is located on the first body portion 18 and one module 26b is located on the second body portion 20. Each module 26a, 26b comprises a compression seal element 28a, 28b and a gripping mechanism in the form of a taper lock 30a, 30b. Each taper lock 30a, 30b includes a lock bowl 32a, 32b mounted on the respective module 26a, 26b and each lock bowl 32a, 32b has a degree of movement relative to the module 26a, 26b. The lock bowls 32a, 32b each define an inclined surface 34a, 34b, each of which is adapted to engage a corresponding inclined or wedge profile surface 36a, 36b on a number of gripping members 38a, 38b.

The gripping members 38a, 38b are adapted to be urged into contact with surfaces 40a, 40b of the body portions 18, 20 to drive the gripping members 38a, 38b radially outwards and into engagement with the pipe 12. A plurality of gripping members 38a and 38b may be provided with respect to each module 26a, 26b and in the embodiment shown in FIG. 1 two are shown.

Each module 26a, 26b defines a boss 42a, 42b and the respective seal element 28a, 28b is located between the respective boss 42a, 42b and lock bowl 32a, 32b. In use, each boss 42a, 42b provides a compression surface 44a, 44b for one of the seal elements 28a, 28b.

In the embodiment shown, the tool 10 is located adjacent to a flanged end 46 of the pipe 12 and the module 26b located adjacent to the end 46 has shorter gripping members 38b to fit inside the pipe 12, though the gripping members may be of any suitable size. The gripping members 38b are aligned with the flanged end 46 such that radial loads applied to the gripping members 38b are applied to the full thickness of the flanged end 46.

The modules 26a, 26b form pistons 48a, 48b (shown most clearly in FIG. 2) that are adapted for axial movement relative to the respective body portion 18, 20. Piston chambers 50a, 50b are defined between the respective body portions 18, 20 and the modules 26a, 26b are adapted to move relative to the body portions 18, 20 in response to a fluid pressure force.

Figure 3:
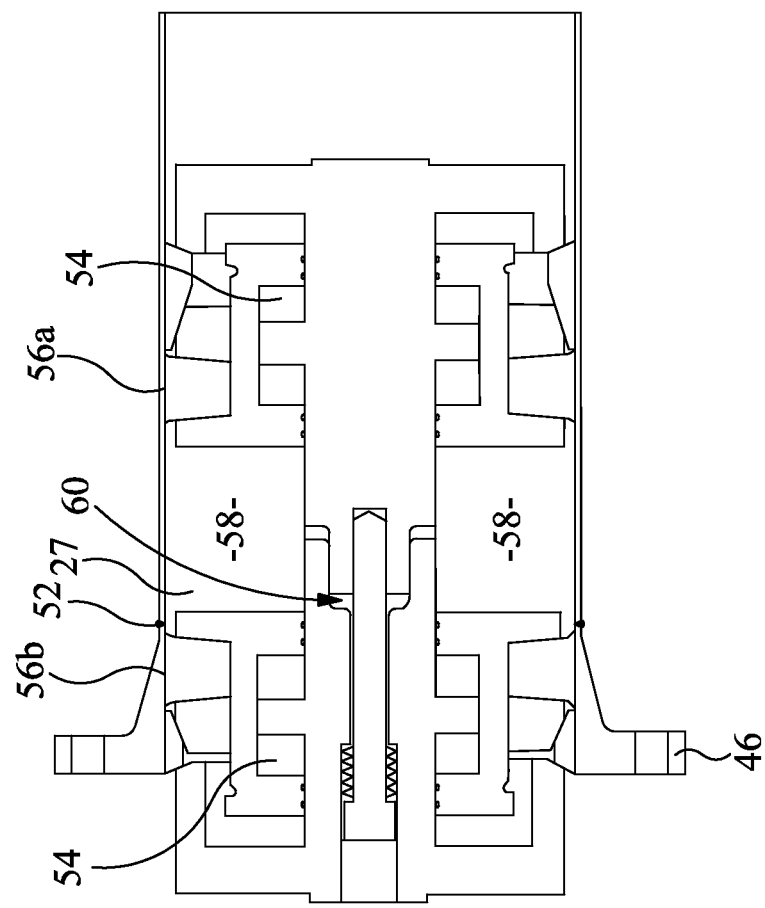
FIG. 3 is diagrammatic cross-sectional view of the tool of FIGS. 1 and 2, shown during application of an axial force.

In reference now to FIGS. 1, 2 and 3 of the drawings, in use, the tool 10 is inserted into the pipe 12 such that it straddles the pipe section 14 to be tested. The tool 10 may be located at any position within the pipe 12 to supply a test pressure to the pipe 12. For example, as shown in FIG. 2, the tool 10 straddles a flange weld 52 and the tool is adapted to test the integrity of the flange weld 52. Location of the tool 10 within the pipe 12 can be achieved accurately and efficiently through use of a centre of gravity bracket (not shown) or the like, the cap screw 22 and spring 24 resisting separation of the body portions 18, 20. In the embodiment shown in the figures, the tool 10 is located adjacent to the flanged end 48 of the pipe 12.

The tool 10 can be located beyond the weld location to provide dual seal isolation from any fluid (not shown) in the pipe 10 to facilitate a welding operation.

Pressurized fluid, such as hydraulic fluid 54, is directed into the piston chambers 50a, 50b to move the modules 26a, 26b axially relative to the respective body portions 18, 20. The lock bowl taper faces 34a, 34b drive the gripping members 38a, 38b radially outwards to engage the tubular bore and the seal elements 28a, 28b are compressed such that sealing surfaces 56a, 56b of the seal elements 28a, 28b are urged into sealing engagement with the pipe 12. The hydraulic load generated by the fluid 54 will be sufficient to generate a secure grip between the tool 10 and the pipe 12 and provides a substantially leak tight seal. The tool 10 thus moves from the disengaged position shown in FIG. 1 to the engaged position shown in FIG. 2.

Once the modules 26a, 26b are set, pressurized fluid 58 is inserted into the outer volume 27 between the seal members 28a, 28b, the body 16 and the pipe 12. It will be understood that the fluid 58 may be inserted into the outer volume 27 and then pressurized to the required test pressure. Alternatively, the fluid 58 may be pressurized to the required level and then inserted into outer volume 27. The modules 26a, 26b are adapted for axial movement in opposite directions such that each gripping member 38a, 38b and each seal member 28a, 28b is pressure assisted by the test pressure generated in the outer volume 27.

Axial loads from the test pressure in the outer volume 27 are transferred through the compression seal elements 28a, 28b, lock bowls 32a, 32b and gripping members 38a, 38b to the pipe 12. This transfers the load efficiently to the pipe 12 but also increases the grip of the lock bowls 32a, 32b and improves the seal by adding compressive load thereto.

The spring 24 is adapted to accommodate any axial movement between the modules 26a, 26b caused by axial strain.

In the event that one or more of the modules 26a, 26b fails to achieve sufficient grip with pipe 12, the modules 26a, 26b will start to separate. However, the cap screw 22 and spring 24 will restrain this movement. Furthermore, a port (not shown) is also provided which is adapted to relieve the test pressure into the inner volume 21 at a pre-determined separation.

Once the outer volume 27 is at test pressure, pressurized fluid 60 is directed into the inner volume 21 to urge separation of the body portions 18, 20. The inner volume 21 is pressurized to the test pressure plus a factor to account for the forces from the retention screw 22 and spring 24. The resultant axial load from the outer and inner test pressures will provide a test load equivalent to pipe bore cross-sectional area multiplied by the test pressure.

Under the influence of the axial force, the tool 10 extends, moving from the position shown in FIG. 2 to the position shown in FIG. 3 (the degree of movement being exaggerated in the Figures). Due to the gripping engagement between the body portions 18, 20 and the pipe 12, the axial separation force is transmitted to the pipe 12 causing a tensile force to be applied to the pipe 12, thereby testing the strength of the pipe section (and/or the weld 52 where appropriate). The separation full force can be applied without over pressurizing the pipe 12.

By monitoring the test pressure while applying the axial test load force, the strength of the pipe 12 may be assessed.

In the event that one or more of the modules 26a, 26b fails to achieve sufficient grip with the pipe 12, the modules will begin to separate. Movement will again be limited by the retention screw 22 and spring 24. Furthermore, a port (not shown) is also provided which is adapted to relieve the inner volume fluid 60 into the outer volume 27 at a pre-determined separation.

On completion of the test, the test pressures may be vented and the body portions 18, 20 are drawn together by the retention spring 24. The tool 10 is then unset by venting fluid 54 from the piston chambers 50*a*, 50*b*.

Those of skill in the art will further recognise that the illustrated apparatus is merely exemplary of the present invention and that the same objectives may be achieved by using a variety of different configurations.

For example, the tool may be hydraulically operated both to activate and de-activate. The sliding sleeve formed by the body portions could take the form of a bi-directional cylinder, a spring return cylinder of the like.

In the embodiment shown in FIGS. 1 to 3, the sliding sleeve is integral to the body as this assists in minimizing the length of the tool. Alternatively, actuation of the tool may be provided by a separate force-generating arrangement mounted or otherwise secured to the body.

Furthermore, though tool activation has been described in relation to pressurized fluid activation, the axial load could be produced by mechanical means such as by applying a torque force to the tool to apply an axial load to the engaging elements.

The tool may be modular in that the engaging elements may be adapted for separate location on the tubular component. Accordingly, an inner module could be pre-set prior to insertion of the outer module, or access to the inner module (the module distal from the pipe end) could be achieved by porting through the outer module (the module nearest the pipe end).

The connection to the modules could include a ball joint or other articulation mechanism to accommodate traversing and testing of non linear sections of pipe including bends.

Accordingly, it will be recognised that where traditionally test tools have sought to minimize axial loads, a tool according to embodiments of the present invention allows full axial force to be applied to the tubular component through gripping members to facilitate efficient localized strength testing and pressure testing for tubular components.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed:

1. A method of testing a tubular component, the method comprising the steps of:
   providing a test tool comprising:
   a first engaging element comprising a lock mechanism and a seal element, wherein the lock mechanism and the seal element of the first engaging element are both adapted for location within the tubular component to be tested and to engage an internal wall of the tubular component to be tested;
   a second engaging element comprising a lock mechanism and a seal element, wherein the lock mechanism and the seal element of the second engaging element are both adapted for location within the tubular component to be tested and to engage an internal wall of the tubular component to be tested;
   a force-generating arrangement adapted to apply an axial tensile test force to a section of the wall of the tubular component via the lock mechanism of the first and second engaging elements while a fluid test pressure is applied to the wall section;
   mounting the test tool within the tubular component to be tested;
   engaging the first and second axially spaced portions of the internal wall of the tubular component with the first and second engaging elements of the test tool;
   applying the fluid test pressure to the wall section of the tubular component between the first and second engaging elements; and
   applying the axial tensile test force to the wall section of the tubular component via the first and second engaging elements, wherein the step of applying the test pressure and the step of applying the axial tensile test force are separate steps.

2. The method of claim 1, further comprising the step of applying a selected axial force to the wall section.

3. The method of claim 1, further comprising the step of monitoring the axial force.

4. The method of claim 1, further comprising the step of monitoring the test pressure.

5. The method of claim 1, further comprising the step of directing pressurized fluid into a volume defined between the first and second engaging elements and the tubular component to provide the test pressure.

6. The method of claim 5, wherein the pressurized fluid inserted into the volume urges the seal elements into engagement with the tubular component.

7. The method of claim 1, wherein the seal elements of the first and second engaging elements are adapted to straddle a portion of the wall of the tubular component to be tested.

8. The method of claim 1, including the step of inserting the test tool into the tubular component and straddling a pipe section to be tested.

9. The method of claim 1, wherein each of the first and second engaging elements of the test tool includes an inclined surface.

10. The method of claim 1, comprising mounting the test tool at any location within the tubular component to be tested.

11. The method of claim 1, wherein the test tool is adapted for mounting within the tubular component at any location.

12. A test tool for use in testing a tubular component and adapted to be mounted within the tubular component to be tested, the test tool comprising:
   a first engaging element comprising a lock mechanism and a seal element, wherein the lock mechanism and the seal element of the first engaging element are both adapted for location within the tubular component to be tested and to engage an internal wall of the tubular component to be tested;
   a second engaging element comprising a lock mechanism and a seal element, wherein the lock mechanism and the seal element of the second engaging element are both adapted for location within the tubular component to be tested and to engage an internal wall of the tubular component to be tested, wherein the first and second engaging elements are adapted to engage axially spaced portions of an internal wall of a tubular component to be tested;
   a force-generating arrangement adapted to apply an axial tensile test force to a section of the wall of the tubular component via the lock mechanism of the first and second engaging elements, wherein the force-generating arrangement is adapted to apply the axial tensile test force to a wall section of the wall of the tubular component via the lock mechanism of the first and second engaging elements while a fluid pressure is applied to the wall section; and a fluid pressure generating arrangement adapted to apply a fluid test pressure to the wall section, wherein an application of the axial tension force and an application of the fluid test pressure are separate steps.

13. The test tool of claim 12, wherein at least one of the first and second engaging elements comprises a gripping mechanism.

14. The test tool of claim 13, wherein at least a portion of the first and second engaging elements is adapted to move axially relative to the tubular component to urge the gripping mechanism into engagement with the tubular component.

15. The test tool of claim 12, wherein the force-generating arrangement is adapted to apply an axial separating force to the first and second engaging elements.

16. The test tool of claim 12, wherein the force-generating arrangement comprises one of, or a combination of, a hydraulic arrangement, a pneumatic arrangement and a mechanical arrangement.

17. The test tool of claim 12, wherein the test tool comprises a body having first and second body portions.

18. The test tool of claim 17, wherein the first and second body portions are axially moveable.

19. The test tool of claim 17, wherein the force-generating arrangement is adapted to apply the axial tensile force to the first and second engaging elements via the first and second body portions.

20. The test tool of claim 17, wherein the first and second engaging elements define a volume between the first and second body portions.

21. The test tool of claim 20, wherein the volume is adapted to receive pressurized fluid.

22. The test tool of claim 21, further comprising a resilient member adapted to urge engagement between the first and second body portions.

23. The test tool of claim 17, wherein the first and second body portions are adapted to be coupled together.

24. The test tool of claim 17, wherein the first and second body portions are adapted for separate location on the tubular component.

25. The test tool of claim 12, wherein the test tool is adapted to define an outer volume between the first and second engaging elements and the tubular component, and the outer volume is adapted to receive pressurized fluid.

26. The test tool of claim 12, wherein the test tool is mounted within the tubular component to be tested.

27. The test tool of claim 12, wherein the test tool is inserted into the tubular component and straddles a pipe section to be tested.

28. The test tool of claim 12, wherein each of the first and second engaging elements of the test tool includes an inclined surface.

* * * * *

UNITED STATES PATENT AND TRADEMARK OFFICE
CERTIFICATE OF CORRECTION

| | | |
|---|---|---|
| PATENT NO. | : 8,935,951 B2 | Page 1 of 1 |
| APPLICATION NO. | : 12/401859 | |
| DATED | : January 20, 2015 | |
| INVENTOR(S) | : Angus George Bowie | |

It is certified that error appears in the above-identified patent and that said Letters Patent is hereby corrected as shown below:

IN THE CLAIMS:

In claim 1, column 8, line 6; after "engaging" delete "the"

Signed and Sealed this
Seventeenth Day of November, 2015

Michelle K. Lee
*Director of the United States Patent and Trademark Office*